(12) United States Patent
Gabbay (10) Patent No.: US 9,980,817 B2
(45) Date of Patent: May 29, 2018

(54) METHOD AND DEVICE FOR CRIMPING AND LOADING HEART VALVE

(71) Applicant: Shlomo Gabbay, Boca Raton, FL (US)

(72) Inventor: Shlomo Gabbay, Boca Raton, FL (US)

( * ) Notice: Subject to any disclaimer, the term of this patent is extended or adjusted under 35 U.S.C. 154(b) by 166 days.

(21) Appl. No.: 14/878,045

(22) Filed: Oct. 8, 2015

(65) Prior Publication Data

US 2017/0100243 A1 Apr. 13, 2017

(51) Int. Cl.
*B25B 27/14* (2006.01)
*A61F 2/24* (2006.01)

(52) U.S. Cl.
CPC .......... *A61F 2/2427* (2013.01); *A61F 2/2409* (2013.01); *A61F 2/2418* (2013.01); *A61F 2310/00011* (2013.01)

(58) Field of Classification Search
CPC ........ B23Q 3/00; B23Q 3/3002; B23Q 1/262; B23P 11/005
See application file for complete search history.

(56) References Cited

U.S. PATENT DOCUMENTS

| | | | |
|---|---|---|---|
| 5,304,182 A * | 4/1994 | Rheinish | A61F 2/167 128/898 |
| 5,935,163 A | 8/1999 | Gabbay | |
| 6,159,200 A * | 12/2000 | Verdura | A61B 17/34 128/897 |
| 6,610,088 B1 | 8/2003 | Gabbay | |
| 7,247,167 B2 | 7/2007 | Gabbay | |
| 7,311,730 B2 | 12/2007 | Gabbay | |
| 7,510,572 B2 * | 3/2009 | Gabbay | A61F 2/2418 623/1.26 |
| 7,530,253 B2 | 5/2009 | Spenser et al. | |
| 7,803,185 B2 | 9/2010 | Gabbay | |
| 8,425,593 B2 | 4/2013 | Braido et al. | |
| 8,438,711 B1 * | 5/2013 | Bissette | B23P 19/027 29/243.5 |
| 8,613,711 B2 * | 12/2013 | Babcock | A61B 10/0038 4/144.2 |
| 8,784,481 B2 | 7/2014 | Alkhatib et al. | |
| 8,845,722 B2 | 9/2014 | Gabbay | |
| 2009/0319037 A1 * | 12/2009 | Rowe | A61F 2/2418 623/2.11 |
| 2011/0251676 A1 | 10/2011 | Sweeney et al. | |
| 2013/0012956 A1 * | 1/2013 | Mirlay | A61F 2/167 606/107 |
| 2017/0100243 A1 * | 4/2017 | Gabbay | A61F 2/2427 |

* cited by examiner

*Primary Examiner* — Lee D Wilson
(74) *Attorney, Agent, or Firm* — Dowell & Dowell, P.C.

(57) ABSTRACT

A method of crimping and loading prosthetic heart valves comprises folding a crimping sheet to form a spiral wrapped around a heart valve; manually rolling and tightening the spiral to compress the valve inside the spiral; inserting the tightened spiral wrapped around the valve into a cannula; and displacing the valve out of the tightened spiral and into the cannula. A kit for crimping and loading the valve into a delivery device comprises a crimping sheet foldable to form a spiral wrapped around the valve, the spiral manually rollable and tightenable to compress the valve wrapped inside the spiral, so that the tightened spiral is slidably insertable into a lumen of a cannula for delivering the valve; and a plunger sized for insertion into the tightened spiral to displace the heart valve out of the spiral and into the lumen of the cannula.

9 Claims, 9 Drawing Sheets

METHOD AND DEVICE FOR CRIMPING AND LOADING HEART VALVE

FIELD

The present invention relates generally to prosthetic heart valves and their implantation, and particularly to devices and methods for loading prosthetic heart valves into a delivery device.

BACKGROUND

Heart valve replacement has become common practice and saves lives.

In order to surgically implant a prosthetic heart valve into a patient, the patient may need to be placed on cardiopulmonary bypass (CPB) during a complicated, but common, open chest procedure. In some cases, however, placing a patient on CPB may pose a significant risk and it may be desirable to avoid doing so if possible. Without CPB, the time available for performing the heart valve implantation is limited and it would be desirable to be able to perform the implantation procedure faster. Even with CPB, it is desirable to reduce the length of time in which the patient is under CPB. If CPB can be completed within a reduced time, it is expected that the patient survival rate can significantly increase and the morbidity can significantly decrease.

Prosthetic heart valves such as collapsible or injectable heart valves can be delivered into a patient's heart using a catheter or trocar. Such a procedure may be done in a less invasive manner than surgical procedures such as open-chest or open-heart surgery, which may be required for delivering non-collapsible heart valves.

There are known techniques for loading the heart valves into a catheter or trocar for delivery of the heart valve into the patient's body. Example devices and procedures are described in U.S. Pat. No. 7,803,185 to Gabbay, entitled "Method of implantation of a heart valve prosthesis through a tubular catheter"; U.S. Pat. No. 7,311,730 to Gabbay, entitled "Support apparatus and heart valve prosthesis for sutureless implantation"; and U.S. Pat. No. 8,845,722 to Gabbay, entitled "Heart valve prosthesis and method of implantation thereof."

It may be necessary to store collapsible prosthetic heart valves in a suitable solution in an uncompressed condition before surgery to maintain and preserve their structural integrity and desired property. It may also be necessary to cool certain prosthetic heart valves just before surgery so that the material becomes resilient and can be compressed and loaded into the delivery device. A known technique for loading a collapsible prosthesis into a delivery device is to push the prosthesis through a funnel attached to the delivery apparatus to gradually compress and reduce the radial size of the compressed prosthesis. An alternative technique is disclosed in U.S. Pat. No. 7,530,253 to Spenser et al., which disclosed a complicated prosthetic valve crimping device capable of reducing the diameter of an expandable prosthetic valve.

Simpler and faster devices and methods for implanting a heart valve are still desirable.

SUMMARY

Accordingly, in one aspect the present disclosure provides a method of crimping and loading a prosthetic heart valve, comprising folding a crimping sheet to form a spiral wrapped around the heart valve; manually rolling and tightening said spiral to compress said heart valve wrapped inside said spiral; inserting an end of the tightened spiral wrapped around the heart valve into a cannula; and displacing the heart valve out of said end of said tightened spiral and into said cannula. The method may further comprise cooling said heart valve and said crimping sheet before said folding. The method may comprise placing a restriction ring around said tightened spiral to prevent loosening of said tightened spiral before said tightened spiral is inserted into said cannula. The crimping sheet may comprise a metal or a plastic. The crimping sheet may have a thickness of less than 1 mm, such as about 0.5 mm. The cannula may be in a trocar. The lumen of said cannula may have a diameter of 1 mm to 40 mm, such as 13 mm to 40 mm. The heart valve may be a sutureless mitral, aortic, tricuspid, or pulmonic valve. The heart valve may be a stented valve. The heart valve may be sized by annuloplasty suturing.

In another aspect, the present disclosure provides a kit for crimping and loading a prosthetic heart valve into a delivery device. The kit comprises a crimping sheet foldable to form a spiral wrapped around the heart valve, said spiral manually rollable and tightenable to compress the heart valve wrapped inside said spiral, so that the tightened spiral is slidably insertable into a lumen of a cannula for delivering the heart valve; and a plunger sized for insertion into said tightened spiral to displace the heart valve out of the spiral and into said lumen of said cannula. The kit may further comprise the cannula, wherein said lumen of said cannula is sized to house the compressed heart valve. The kit may further comprise a restriction ring sized to slide over said tightened spiral to prevent loosening of said tightened spiral. The crimping sheet may comprise a metal or a plastic. The crimping sheet may have a thickness of less than 1 mm, such as about 0.5 mm. The cannula may be in a trocar. The lumen of said cannula may have a diameter from 1 mm to 40 mm, such as from 13 mm to 40 mm. The kit may comprise a plurality of cannulas having different lumen diameters. The lumen diameters may be selected from 18, 21, 23, 24, 25, 27, 29, 31, 33, and 35 mm. The heart valve may be a stented sutureless mitral, aortic, tricuspid, or pulmonic valve.

Other aspects, features, and embodiments of the present disclosure will become apparent to those of ordinary skill in the art upon review of the following description of specific embodiments in conjunction with the accompanying figures.

BRIEF DESCRIPTION OF THE DRAWINGS

In the figures, which illustrate, by way of example only, embodiments of the present disclosure.

DETAILED DESCRIPTION

In overview, it has been realized that a manually rollable crimping sheet can be used to quickly crimp or compress a prosthetic heart valve and load it into a trocar. The insertion can be completed in seconds or within about 2 minutes.

Figure 1:
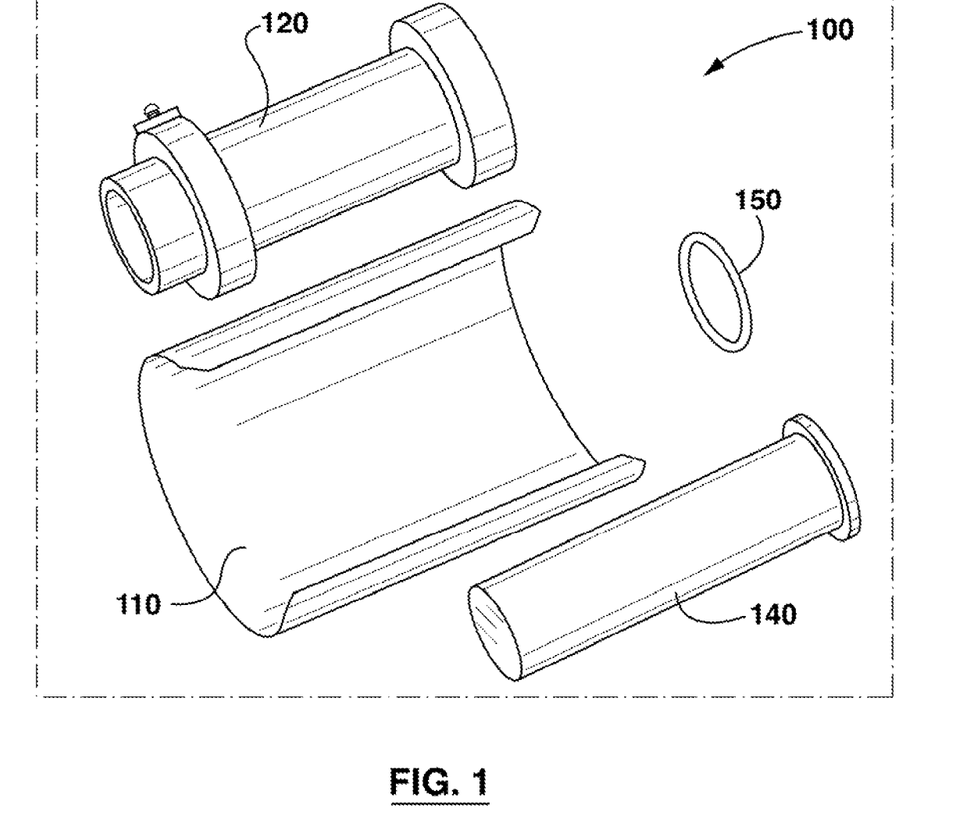
FIG. 1 is a perspective view of components in a tool kit for crimping and loading heart valves, illustrative of an embodiment of the present disclosure.

FIG. 1 illustrates an embodiment of the present disclosure, which is a tool kit 100, for crimping and loading a heart valve (not shown in FIG. 1, but see FIG. 2) into a trocar (not fully shown). Tool kit 100 includes a crimping sheet 110, a cannula 120, a plunger 140, and a restriction ring 150.

Figure 2:
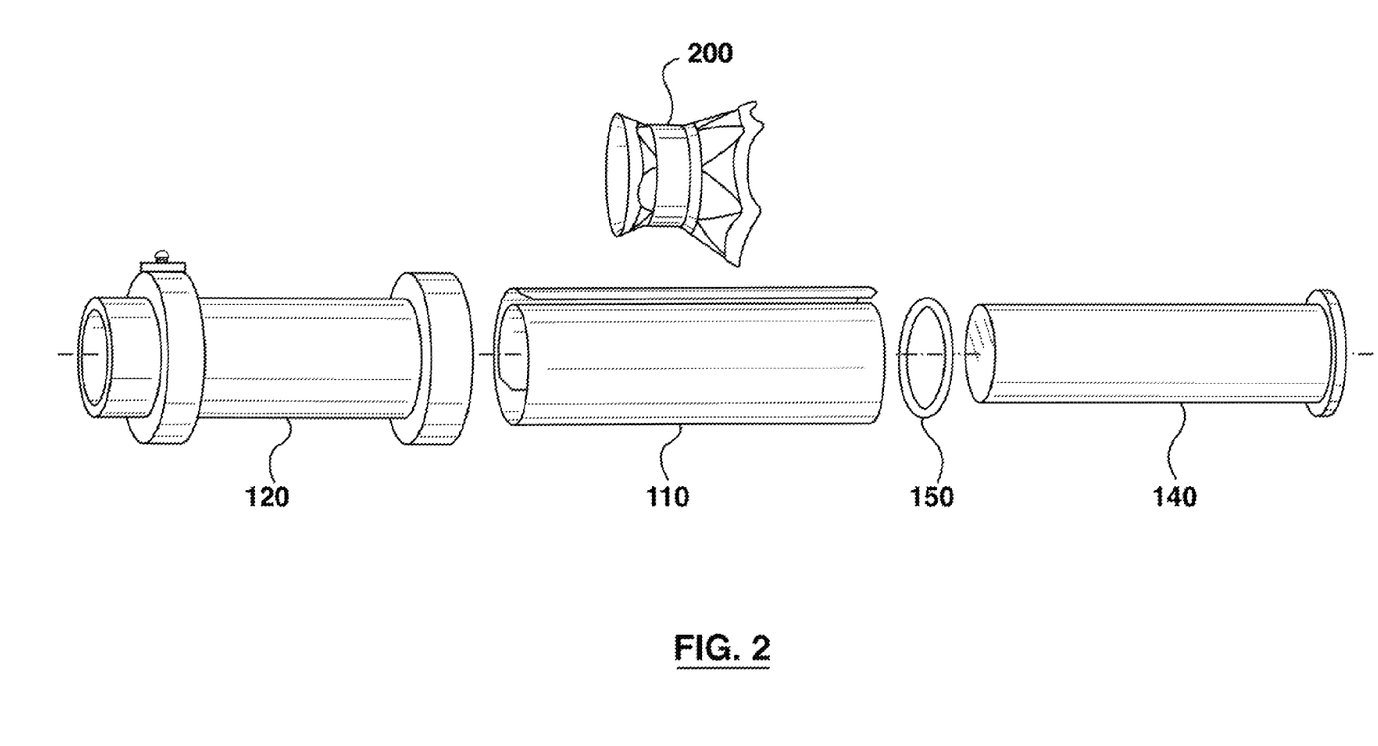
FIG. 2 is a perspective view of the components of the tool kit of FIG. 1, aligned for loading a heart valve.
Figure 14:
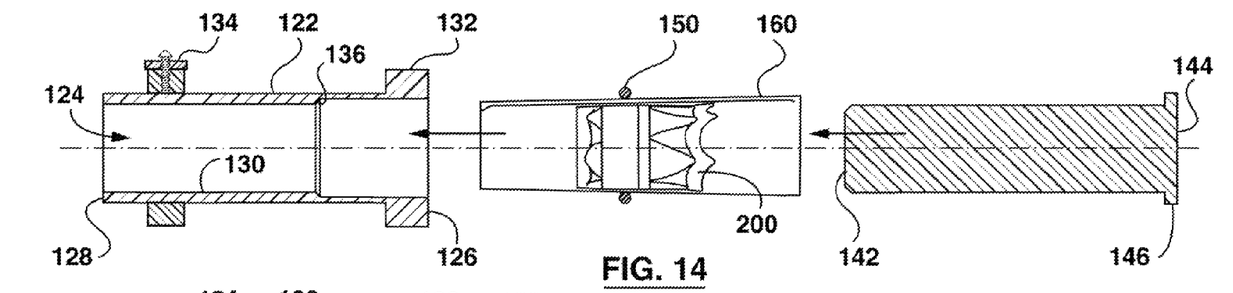
FIGS. 14, 15, 16 and 17 are cross-sectional views of the assemblies shown in FIGS. 6, 7, 9, and 10 respectively.
Figure 15:
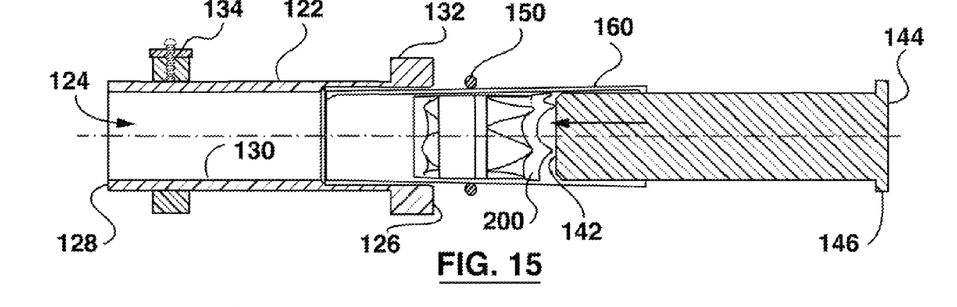
Figure 16:
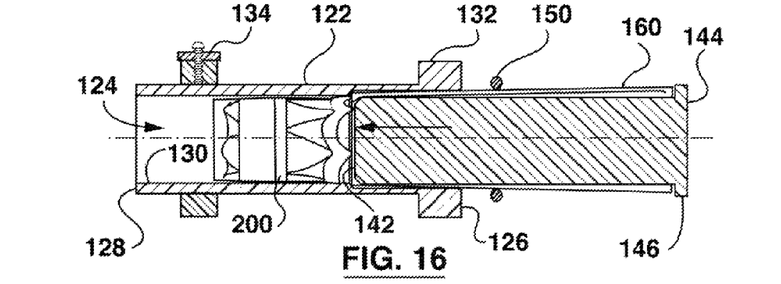

FIG. 2 illustrates the general alignment of crimping sheet 110, cannula 120, plunger 140 and restriction ring 150 of tool kit 100 during use for delivering a prosthetic heart valve 200. Schematic cross-section views of crimping sheet 110, cannula 120, plunger 140 and restriction ring 150 are shown in FIG. 14. The axial direction of cannula 120 or plunger 140 is indicated in the figures by the dot-dash line along the axial direction. A radial direction refers to a direction that is perpendicular to the axial direction, as can be understood by those skilled in the art.

Crimping sheet 110 may be made of a resilient material that is rollable by hand and is strong enough to hold a compressed prosthetic heart valve in the rolled sheet. For example, suitable materials may include plastic or metal sheets. Suitable metals may include aluminum, stainless steel, a suitable alloy or composite, or the like. Crimping sheet 110 may be less than 1 mm thick, such as about 0.5 to about 1 mm thick. The size of crimping sheet 110 may vary depending on the size of the heart valve to be loaded and the lumen diameter and the length of cannula 120. Typically, crimping sheet 110 may be square shaped with a size of about 13×13 cm. Crimping sheet 110 may also be rectangular shaped or have another shape. The size of crimping sheet 110 may be selected such that a user is able to fold and roll crimping sheet 110 with both hands conveniently. The short side of a rectangular shaped crimping sheet may be about 12 cm to about 15 cm. The sizes of crimping sheets may of course vary depending on a number of factors, and it is possible to include a number of crimping sheets with different sizes in one kit. For smaller valves, crimping sheet 110 may have a correspondingly smaller size. For larger valves, crimping sheet 110 may have a correspondingly larger size. In some embodiments, crimping sheet 110 may be formed of a material that retains at least some of its resiliency when it is cooled to below room temperature, the reasons for which will become clear below.

Cannula 120 may have any standard or conventional shape and size, and may be made of any known material suitable for forming cannula of trocars for delivery heart valves. FIG. 1 illustrates an example embodiment of cannula 120, and a possible cross-sectional view of the example cannula 120 is illustrated in FIG. 14. It should be understood that, however, other types of cannula may also be used, which may have different shapes and sizes and may have different or additional features or functions. As better seen in FIG. 14, the example cannula 120 may have a cylindrical tubular body 122 with a lumen 124 extending between the ends 126, 128 of cannula 120. For inserting typical heart valves, cannula 120 may have a length (L) of about 13 cm, and a lumen diameter (D) of about 13 mm to about 35 mm, such as 13, 15, 17, 19, 21, 23, 25, 27, 29, 31, 33, or 35 mm. Depending on the materials used in the heart valve, it can be expected that smaller or larger lumen diameters for cannula 120 may also be possible, such as from about 1 mm to about 13 mm, or from about 35 to about 40 mm. As will be further discussed below, while FIG. 1 depicts only one cannula, kit 100 may include multiple cannulas for use with heart valves of different types and sizes. Lumen 124 may be stepped or tapered, for reasons that will be discussed below. For example, as depicted in FIG. 14, lumen 124 in cannula 120 may have a step 136, such that the lumen diameter at the section between end 126 and step 136 is larger than the lumen diameter at the section between end 128 and step 136.

Figure 21:
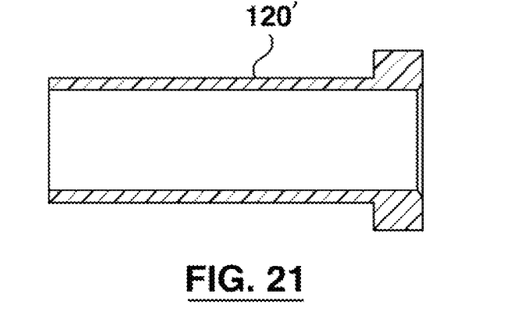
FIGS. 21 and 22 are cross-sectional views of different cannulas.
Figure 22:
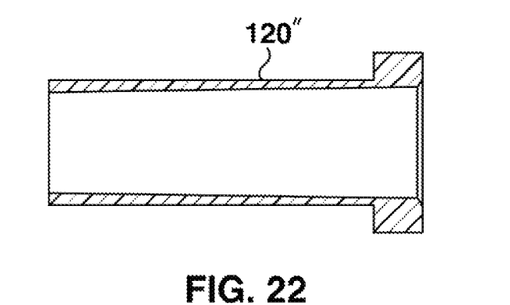

Alternatively, in different embodiments, a cannula with no step in the lumen, such as cannula 120' illustrated in FIG. 21, may be used. An example cannula 120" with a tapered lumen is illustrated in FIG. 22. Tool kit 100 may include two or more of cannulas selected from cannulas 120, 120', 120".

While not specifically depicted in the figures, an end portion, e.g. at end 128, of cannula 120 may be shaped for coupling with a heart valve delivery device, or include a coupling attachment or device for coupling cannula 120 to the delivery device. The delivery device may be a trocar or catheter. The trocar may be an atrial injector. Alternatively, cannula 120 may be an integral part of a trocar. Cannula 120 may be made of ceramic, plastic, metal, a polymer, a composite material, or other materials that are known to be suitable for delivering heart valves. Lumen 124 has a relatively smooth inner surface 130 so that a heart valve inserted into lumen 124 can slide in lumen 124 and be conveniently pushed through lumen 124 without being damaged. Inner surface of lumen 124 may be coated with a coating material selected to provide reduced friction and increased durability.

When screw 138 is untightened, flange 134 is slidable along the cannula body so its position on cannula 120 is adjustable. Flange 134 can be fixed at a selected position by tightening screw 138. This position adjustment can be used to assist the surgeon to determine the depth of insertion and at which the heart valve is to be discharged from cannula 120. That is, for a given position of flange 134 on cannula 120, the distance from end 128 to flange 134 can be used to judge the depth in the body of the patient at which the heart valve will be discharged from cannula 120. A valve manufacture may suggest a suitable depth for its specific valves. This indication of depth may be helpful for implanting a heart valve in a mitral position.

In an alternative embodiment, flange 134 may be omitted. For example, for implanting a valve in an aortic position, it is not necessary to have flange 134. The outer diameter of such a cannula can be uniform throughout, or increase slightly and gradually towards one end.

Flange 132 may be provided for convenient grip and handling by the user. For example, the user may hold flange 132 with two fingers (such as the index and middle fingers) while pushing plunger 140 into cannula 120 with another finger (such as the thumb), similar to operating a typical syringe.

Plunger 140 has a generally cylindrical shape with a diameter selected for insertion into cannula 120. The diameter of plunger 140 is smaller than the lumen diameter of cannula 120 by a suitable amount as will be become apparent below. For example, the diameter of plunger 140 may be smaller than the lumen diameter of cannula 120, such as by about 0.5 mm. Plunger 140 may have a generally uniform diameter through its length, or may have varying diameters.

The length of plunger 140 may be selected based on the length of cannula 120. In some embodiments, plunger 140 may be longer than cannula 120 by about 1 to 5 cm.

As better seen in FIG. 14, plunger 140 may have generally flat ends 142 and 144. In some embodiments, one end of plunger 140 may optionally have a stopper or flange 146, as illustrated in FIGS. 1 and 14, for preventing over insertion of plunger 140 into cannula 120 as will be further discussed below.

Figure 23:
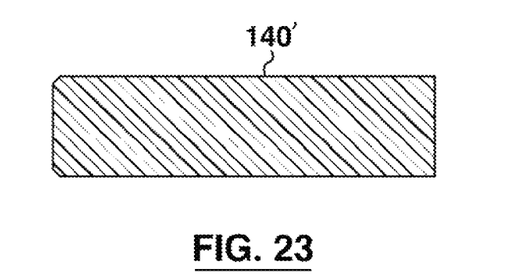
FIGS. 23 and 24 are cross-sectional views of different plungers.

In different embodiments, the shape and size of the plunger may be modified or varied. For example, a plunger with a simple cylindrical shape without an end flange may also be used. The cross-section of an example alternative plunger 140' is illustrated in FIG. 23.

Figure 24:
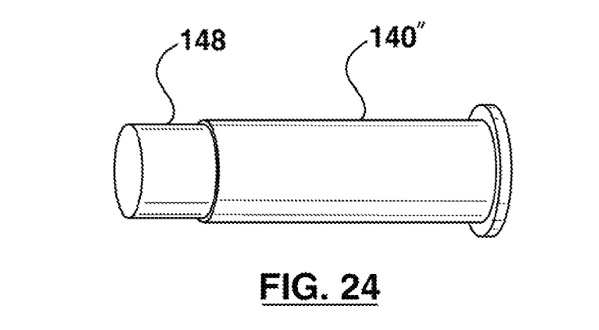

A plunger may also have a terminal end with a reduced diameter, as illustrated in FIG. 24. As depicted, a plunger 140" has a front end section 148 with a reduced diameter, as compared to the diameter of the middle and rear section of plunger 140". Plunger 140" may be convenient to use for loading heart valves with a non-compressible valve portion and compressible stents made of nickel titanium (nitinol). Front end section 148 may be about 2 cm to about 3 cm long and have a diameter reduced by, e.g., about 1 or 2 mm, as compared to the larger diameter at the middle or rear section of plunger 140". During use, front end section 148 of plunger 140" can contact the central portion of the valve, but not the peripheral (umbrella) portions of the valve near the lumen wall of cannula 120. This may allow the valve to be loaded without over-compressing or crushing the nickel titanium material.

Tool kit 100 may include two or more plungers 140, 140' and 140".

Plunger 140 may be formed of any suitable material that has the required mechanical strength and rigidity.

Restriction ring 150 may be a rubber band, or made of any suitable elastic material. Restriction ring 150 has a normal size smaller than the lumen diameter (D) of cannula 140, but can be placed over a cylindrical object having the same diameter D and exert a restriction pressure on the cylindrical object. The purpose and function of restriction ring 150 will become clear below. Optionally, when multiple cannulas are included in kit 100, restriction ring 150 may be selected so it can be used with each of the cannulas. Alternatively, multiple restriction rings may be included in kit 100. While an elastic restriction ring may be convenient to use, in some embodiments, restriction ring 150 may be non-elastic but has inner diameter that matches, but is slightly smaller than, the lumen diameter of cannula 140. While as depicted in FIG. 14, restriction ring 150 has a generally circular cross-section, in different embodiments, restriction ring 150 may have another cross-sectional shape, such as a rectangular or oval shape.

For simplicity, it is assumed cannula 120, plunger 140 and restriction ring 150 are radially symmetrical with the exception of flange 134 and screw 138. However, in different embodiments, portions or sections of cannula 120, plunger 140 and restriction ring 150 may be modified and be non-symmetrical.

In use, kit 100 can be utilized to conveniently crimp and load a prosthetic heart valve into a heart valve delivery device such as a trocar or a catheter (not separately shown).

The heart valve may be a stented valve or a stentless valve. Typically, the heart valve may be a sutureless valve, although kit 100 may also be used for loading a sutured valve. The heart valve may be a mitral, aortic, tricuspid, or pulmonic valve. Conveniently, a heart valve integrated with a compressible stent may be loaded using kit 100.

Before crimping and loading the heart valve, the heart valve and components of kit 100 may be prepared and pretreated, such as being cooled or sanitized, or both. The patient to receive the heart valve is also properly prepared for the procedure to be performed.

For example, in some cases, the heart valve and crimping sheet 110 may be cooled to below room temperature by immersing them in ice water.

Figure 3:
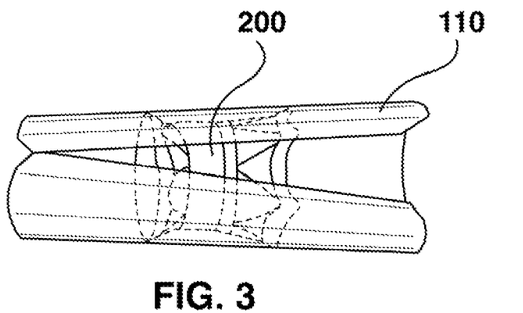
FIG. 3 is a perspective view of the crimping sheet shown in FIG. 1 being wrapped around the heart valve shown in FIG. 2.

As illustrated in FIG. 3, just before the time for heart valve delivery during a heart surgery, the surgeon or an assistant of the surgeon (referred to as the operator herein after) places a properly prepared heart valve 200 on crimping sheet 110, which can be performed manually using the operator's hands.

Figure 4:
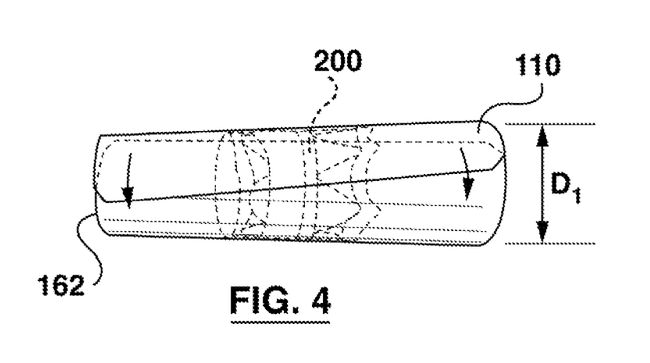
FIG. 4 is a perspective view of the crimping sheet wrapped around the heart valve, as shown in FIG. 3, after being rolled into a spiral.
Figure 5:
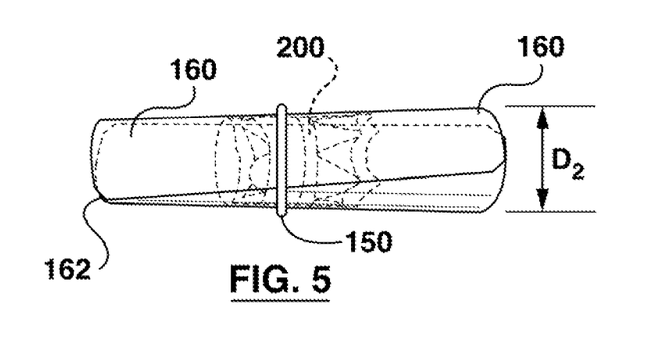
FIG. 5 is a perspective view of the spiral of FIG. 4, being further rolled to reduce its diameter, and inserted into the restriction ring shown in FIG. 1.
Figure 6:
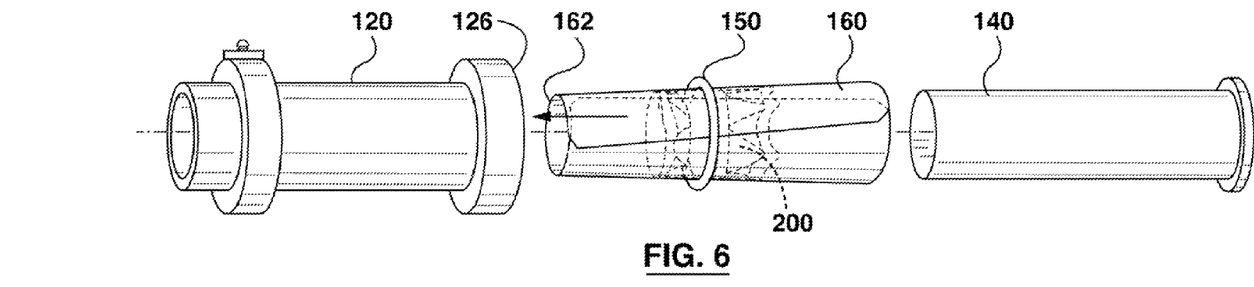
FIG. 6 is a perspective view of the spiral of FIG. 5 aligned for insertion into the cannula shown in FIG. 1.
Figure 7:
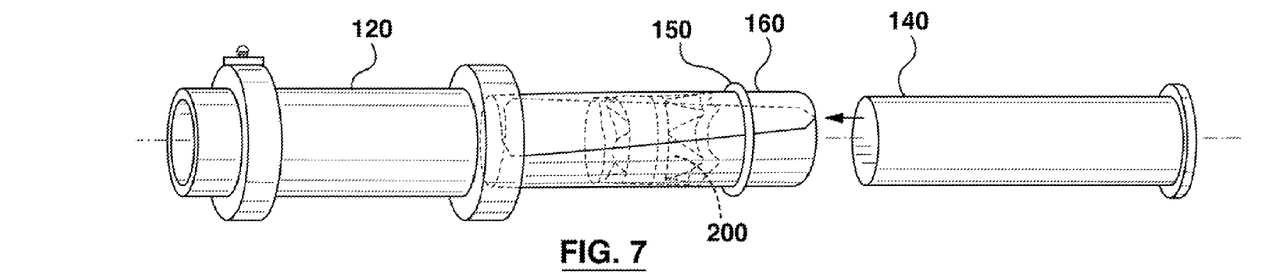
FIGS. 7, 8, and 9, are perspective views of the spiral and cannula of FIG. 6 and the plunger shown in FIG. 1, illustrating insertion of the spiral and plunger into the cannula to displace the heart valve out of the spiral and into the cannula.
Figure 8:
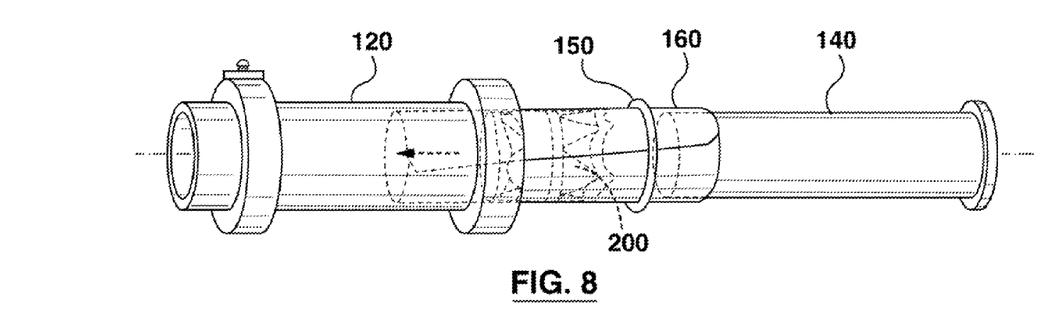
Figure 9:
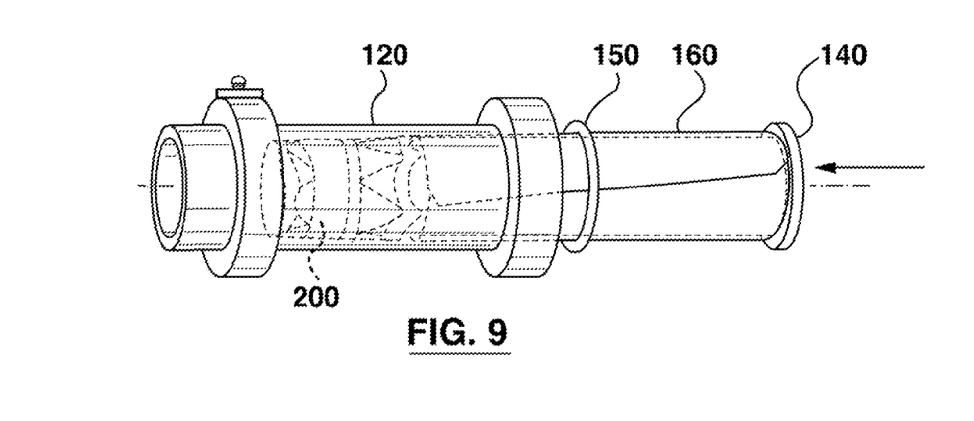

As illustrated in FIGS. 4 and 5, crimping sheet 110 is then folded and rolled to form a tubular spiral 160 wrapped around heart valve 110. Initially, the diameter of the spiraled crimping sheet 110 may be slight larger than the normal radial size of heart valve 110 in an uncompressed state, as illustrated in FIG. 4. The initial diameter ($D_1$) of the spiraled crimping sheet 110 may be manually reduced (by hand) by rolling and tightening the spiraled crimping sheet 110, with frictional force applied by fingers of the operator (not shown for simplicity), as illustrated by the arrows shown in FIG. 4. This rolling and tightening of spiral 160 will compress the heart valve and reduce the diameter of spiral 160 to $D_2$, which is smaller than the lumen size of cannula 120, as illustrated in FIG. 5, so that an end 162 of spiral 160 can be conveniently inserted into lumen 124 at an end 126 of cannula 120 (see FIG. 7 below).

When crimping sheet 110 is folded and rolled around heart valve 200, it forms a "spiral". As used herein, the term "spiral" refers to any rolled sheet that has at least a portion of the sheet overlapping another portion of the sheet so that the outside portion of the sheet is farther away from a central point than the inside portion of the sheet. The overlapping portions may include multiple layers of the sheet or may include an outer layer partially overlapping an inner layer.

As depicted in FIG. 5, restriction ring 150 may be placed over the tightened spiral 160 to maintain spiral 160 in the tightened state and its reduced diameter.

As can be appreciated, when crimping heart valve 200 with crimping sheet 110 to form spiral 160, the initial spiral 160 does not need to have a cylindrical shape, but may have a slightly tapered shape or trapezoidal profile. The final shape of spiral 160 may be easily adjusted by hand, and may also be automatically assumed when spiral 160 is placed inside restriction ring 150.

Next, as illustrated in FIGS. 6, 7, 8, 14 and 15, end 162 of spiral 160 is aligned and inserted into lumen 124 at end 126 of cannula 120, while heart valve 200 is still wrapped inside spiral 160. In the figures the directions of relative movement of the moving parts are indicated with the arrows shown. Spiral 160 may be manually inserted to a suitable depth selected by the operator. Alternatively, where a step 136 is provided in lumen 160, spiral 160 may be inserted until end 162 touches and abuts step 136, as can be better seen in FIG. 15. Conveniently, step 136 may function as a stopper to prevent over insertion of spiral 160. Further, the operator does not have to judge when to stop and can move more quickly and easily determine that the right depth has been reached when spiral 160 abuts step 136.

Next, as illustrated in FIGS. 8, 9, 15, and 16, plunger 140 is inserted into spiral 160 to displace heart valve 200 out of tightened spiral 160 and into lumen 124 of cannula 120.

It can be understood that to dislodge heart valve 200 from spiral 160, heart valve 200 may be pushed in with plunger 140 while spiral 160 is held in place. Alternatively, with a longer plunger than as depicted in the figures, it is also possible to hold the inserted plunger in place while it is abutting heart valve 200 and simultaneously pull spiral 160 out of lumen 124 of cannula 120.

Figure 10:
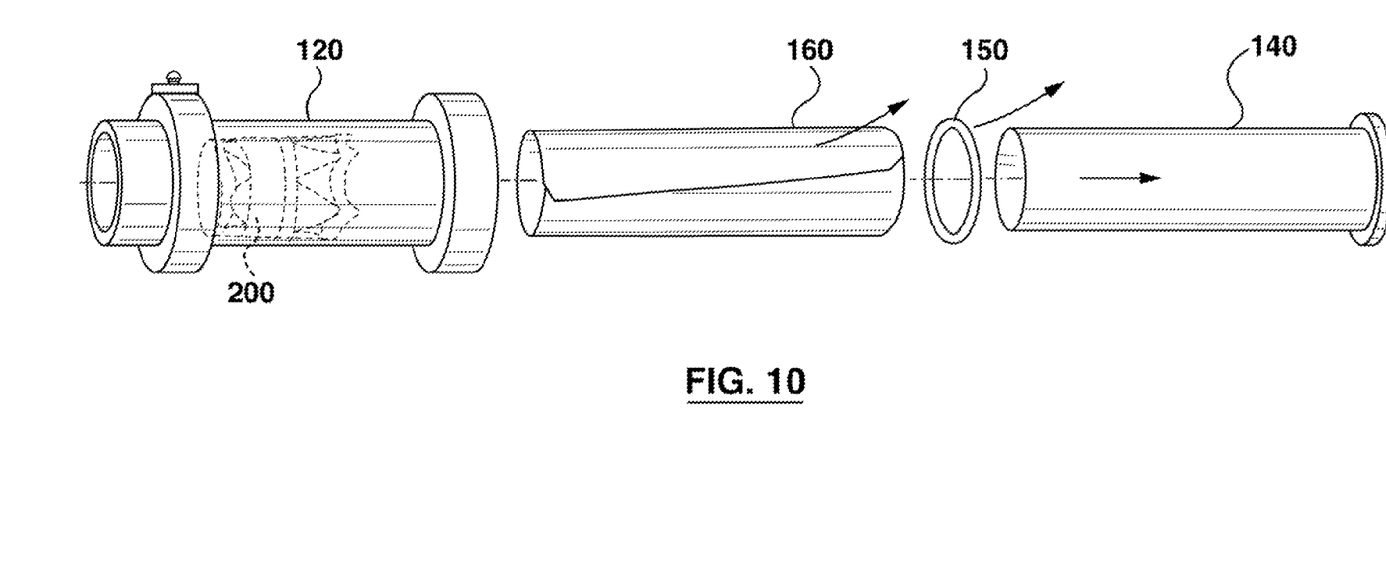
FIG. 10 is a perspective view of the spiral, cannula and plunger shown in FIG. 9 but after the spiral and plunger has been withdrawn from the cannula.
Figure 11:
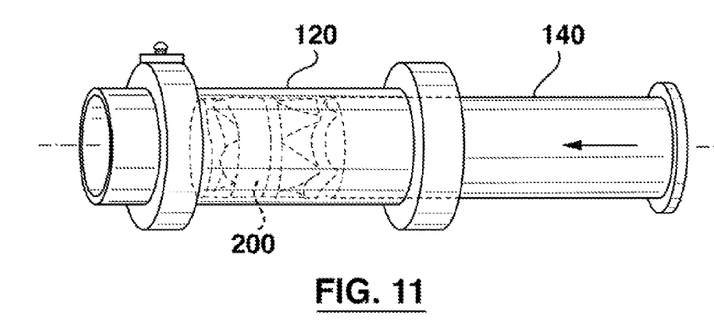
FIGS. 11, 12, and 13 are perspective views of the cannula, the heart valve, and the plunger shown in FIG. 10, illustrating re-insertion of the plunger into the cannula to displace the heart valve out of the cannula.
Figure 17:
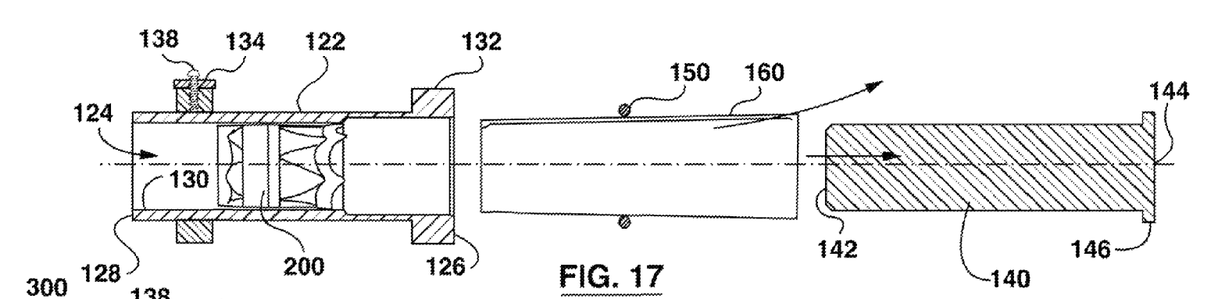
Figure 18:
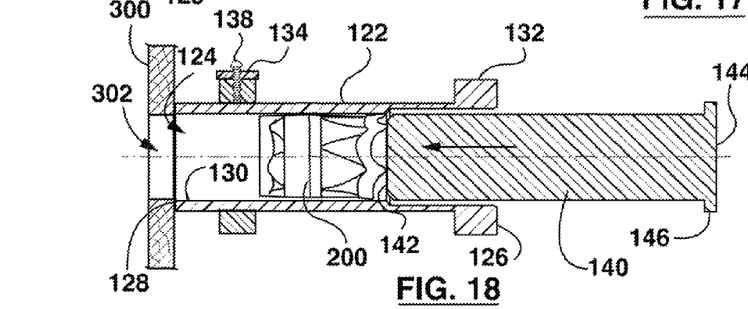
FIGS. 18, 19, and 20 are cross-sectional views of the cannula, heart valve, and plunger arranged as in FIGS. 11 to 13, illustrating a process of inserting the heart valve into a heart opening from the cannula.

As illustrated in FIGS. 10 and 17, plunger 140 and spiral 160 can then be retrieved or withdrawn out of cannula 120. Heart valve 200 in cannula 120 is now ready to be delivered either directly into the patient's heart or to another delivery or surgical device.

Before heart valve 200 is injected into a patient's body from cannula 120, heart valve 200 and cannula 120 may be immersed in warm saline to allow heart valve 200 to resume its room temperature properties.

The entire loading procedure can be conveniently performed with two hands of the operator, and can be performed quickly, such as in seconds or within two minutes.

Delivering heart valve 200 in cannula 120 to the patient's heart or to another delivery or surgical device can be performed in any known or convention manner, as can be understood by those skilled in the art, and will not be comprehensively described herein.

FIGS. 11 to 13 and 18 to 20 schematically illustrate a possible procedure to deliver heart valve 200 from cannula 120 to a heart opening 302 of a heart 300 (only schematically and partially shown). Briefly, plunger 140 may be re-inserted into cannula 120 from end 126 to push heart valve 200 out of cannula 120, as depicted. Alternatively, plunger 140 may be re-inserted into cannula 120 from end 128, depending on how heart valve 200 is oriented when loaded and which end of cannula 120 is suitable for contacting the delivering device or the heart tissue.

Figure 12:
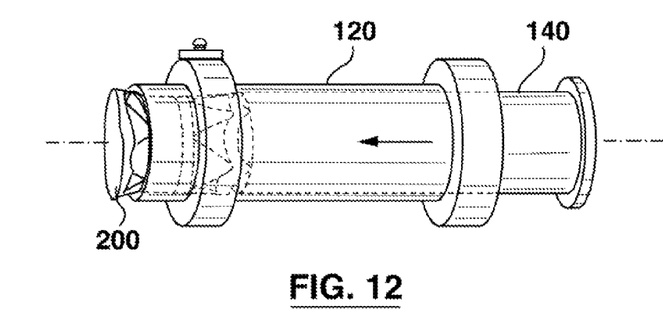

As depicted in FIG. 12, the ventricular portion of the heart valve (which may be a ventricular stent) may be first pushed out of cannula 120 and the atrial stent of heart valve 200 may remain inside cannula 120 at this point. At this point, the ventricular stent expands, but the atrial stent is still compressed.

Figure 13:
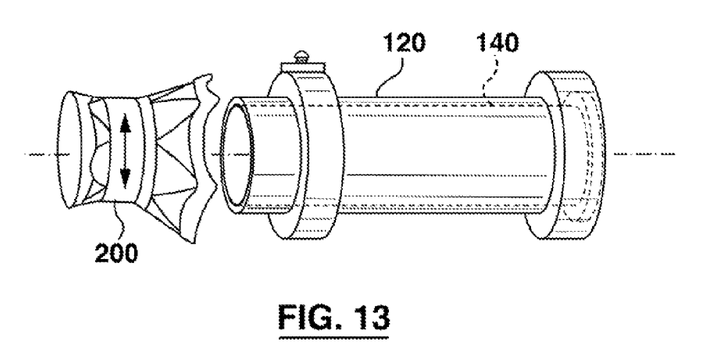

When heart valve 200 is completely pushed out of cannula 120, the atrial stent of heart valve 200 will also expand, as illustrated in FIG. 13. As is typical, the atrial stent may be larger than the ventricular stent when fully expanded as illustrated in FIG. 13. The expanded stents can prevent heart valve 200 from being dislocated due to flow pressure, as better illustrated in FIGS. 19 and 20. Certain stented valves may be designed such that a higher flow pressure will actually increase the press against the stent so as to hold the valve tighter.

When heart valve 200 is pushed out of lumen 124 of cannula 120 (or another delivery device, not shown), it becomes un-compressed and resumes its original shape and size. Due to this change of its stent structure, heart valve 200 can be conveniently inserted into opening 302 and be securely implanted and held at opening 302 of heart 300, as can be better seen in FIG. 20.

Figure 19:
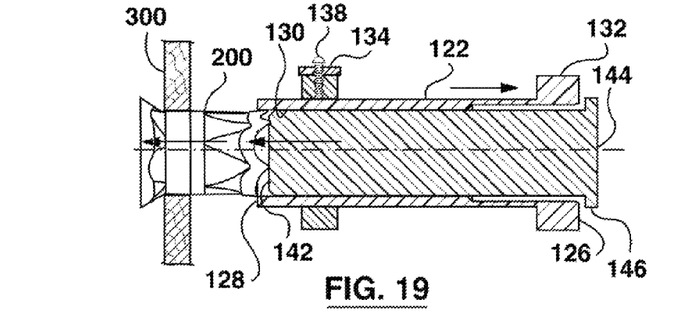
Figure 20:
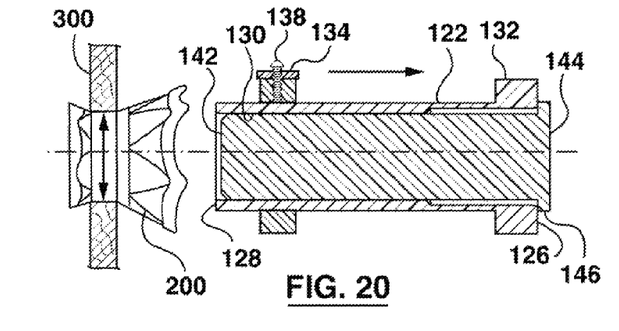

To withdraw cannula 120 after heart valve 200 has been inserted into opening 302, plunger 140 may be held in place, or remain pushed against valve 200, and the tubular body 122 may be slid back as shown in FIG. 19. Alternatively, such as when heart valve 200 has a compressible and expandable ventricular stent, which expands after being pushed through opening 302, as illustrated in FIG. 19, cannula 120 and plunger 140 may be pulled out together, as the expanded ventricular stent of valve 200 can abut the edge of opening 302 to prevent axial movement of valve 200 with the withdrawn cannula 120 and plunger 140.

During an actual heart procedure, the implanted heart valve may be resistant to flow pressure and be held in place by the compressible and expandable stents, or alternatively by suture.

When implanting a heart valve with a ventricular stent, the ventricular stent may be pushed out of cannula 120 first as illustrated in FIG. 12, so that the valve attached to the ventricular stent may be anchored in the ventricular annulus (schematically represented by opening 302).

If opening 302 or the annulus is much larger than the valve size, e.g., the lumen diameter is above 33 mm for a 33 mm valve, the surgeon, before inserting the valve, may perform annuloplasty suturing to tie, e.g., a 33 mm sizer around the valve, or around the trocar (injector) itself.

The illustrated example may be appropriate for implanting a heart valve into a mitral annulus. For implanting a heart valve in the aorta, orientation of the valve or the cannula may need to be reversed. In this case, the inflow may be downward and the ventricular stent (inflow stent) is significantly smaller and the stent last inserted into the aorta may be bigger. The flanges of the stent may be sutured to the aorta with, for example, three stitches, one on each flange. This procedure can be performed quickly to reduce morbidity and mortality. In this procedure, a valve disclosed in U.S. Pat. No. 5,935,163 or sold under the name Versaflex™ may be suitable, but other types of valves may also be used.

As can be appreciated, the loading procedure is a relatively simple procedure and the operator can quickly learn how to properly use kit 100 and load a heart valve. No complicated devices are required and kit 100 is versatile and can be used with different types or kinds of valves. In particular, a heart valve may be crimped and loaded conveniently with two hands using kit 100 without any additional instrument. In some embodiments, however, an additional instrument or device may be used or provided to facilitate crimping the heart valve with one or two hands.

Different heart valves may have different sizes and may require different lumen sizes. Conveniently, if multiple cannulas are provided, a suitable cannula can be selected for a given heart valve quickly. In some embodiments, however, collapsible heart valves of different sizes may be loaded with the same cannula 120. In any event, the same crimping sheet 110 may be conveniently used for different valves, although it is also possible to provide multiple crimping sheets that fit better with different valves or cannulas.

A prosthetic heart valve to be delivered may be a collapsible heart valve prosthesis known in the art, such as those disclosed in U.S. Pat. Nos. 8,845,722; 8,784,481; or 8,425,593. A heart valve that can be loaded with kit 100 can have a stent or another collapsible support structure and a valve portion positioned within the support structure. The heart valve can be a mitral valve, aortic valve, or another kind of valve. Typically, the heart valve may be of a generally tubular shape, with an inflow end and an outflow end. The heart valve may be radially compressed from a first un-collapsed state into a second collapsed state. The heart valve has a smaller reduced axial cross section in the collapsed state than it does in the un-collapsed state. The heart valve can be self-expandable after being inserted into the patient or it may be expanded by another instrument or apparatus. The expanded heart valve prosthesis can engage with the adjacent tissue to mitigate axial movement, the prosthesis may be held in place by sutures or any other fastening means. In some embodiments, the heart valve may be sutureless.

Example heart valves may include VERSAFLEX™ valves, BIOMITRAL™ valves or BIOAORTIC™ valves, or semi-stented aortic valves.

When kit 100 is used to deliver compressible heart valves, a single cannula can be selected for use with different valves with different sizes. When the heart valves to be delivered are stented, and optionally sutureless, different cannulas with different lumen diameters may need to be used depending on the sizes of the valves. For example, typical heart valves may have radial sizes or diameters of 15 to 33 mm, such as, 15, 17, 21, 23, 25, 27, 29, 31, and 33 mm. The valves may also have even larger or smaller sizes. For aortic valves, the valve sizes may be 15 to 29 mm. For BIOMI-TRAL valves, currently available sizes are 25 to 33 mm.

As can be appreciated, a typical apical trocar may have a lumen diameter of about 10 to about 18 mm. An atrial injector or trocar may have a larger diameter since it does not need to go through the apex and the atrium is relatively larger. For installing valves in the mitral position through the atrium with CPB, the lumen size of the cannula may need to be much larger, i.e., about 25 to about 35 mm.

It is possible to use a cannula with a larger lumen size to deliver smaller valves if the valves are tied with a sizer. As can be appreciated, techniques for sizing a heart valve or annuloplasty are known to those skilled in the art and will not be described further herein.

When a heart valve is implanted without CPB from the apex of the heart (either left or right side), the crimped valve can be reduced to a smaller size, as illustrated in U.S. Pat. No. 7,510,572 (see e.g. FIG. 19 thereof).

A loading procedure described herein can be used with exiting valves that have been clinically proven to work well. For example, it is possible to implant existing porcine or pericardial valves without sutures and without modification to the valves. For instance, heart valves described in U.S. Pat. Nos. 6,610,088; 8,845,722; 5,935,163; 7,247,167; or 7,311,730 may be implanted using a procedure described herein or using a tool kit described herein.

When a mitral valve is to be implanted without CPB, a procedure described herein may be modified and combined with a procedure described in U.S. Pat. No. 8,845,722. Alternatively, a stented sutureless valve in mitral position can also be implanted with CPB, when a loading procedure described herein is used, through the atrium.

It is not necessary that the entire valve or valve assembly is compressible. In some cases, the valve itself may be formed of a non-compressible material and is attached to a compressible stent. The stent materials may be compressible only when they are cooled to below room temperature.

Kit 100 can be repeatedly used, although cleaning or re-sanitization may be required before re-use.

As now can be understood, crimping sheet 110 should be large enough so it can completely envelope heart valve 200. When two opposite edges of crimping sheet 110 are folded around to meet one another, crimping sheet 110 should form a generally a cylindrical shape due to its resiliency and mechanical strength. The open channel in the folded crimping sheet 110 is preferably large enough to receive heart valve 200 in a non-compressed state.

Crimping sheet 110 may be pliant and resilient such that it is easy to wrap and fold it around heart valve 200, and yet it has sufficient strength to maintain a generally cylindrical or spiral shape, even if a friction force and a pressure are applied unevenly to the rolled-up spiral to tighten it. Crimping sheet 110 should also have sufficient strength to protect heart valve 200 from damages during handling and operation when heart valve 200 is wrapped inside spiral 160.

Conveniently, if plunger 140 is provided with a stopper flange 146, it can be inserted until flange 146 abuts end 126 of cannula 120, to prevent over insertion.

As now can be appreciated, while restriction ring 150 is convenient to use, it is not necessary to include it in the tool kit. In some embodiments, spiral 160 can simply be held in the hand before insertion into cannula 120 without the use of a restriction ring to keep the spiral in shape.

In one embodiment, a tool kit for crimping and loading a prosthetic heart valve into a delivery device includes one or more crimping sheets, each rollable to form a spiral that can compress the heart valve, one or more cannulas each having a lumen for receiving and delivering the heart valve, and one or more plungers for displacing the heart valve. The crimping sheets, cannulas, and plungers may include any example crimping sheet, cannula, or plunger described herein. In an embodiment, the crimping sheet includes a material such that it is elastic enough to be rolled around a prosthetic heart valve of various sizes yet rigid enough that it can maintain its structure as a tubular spiral with an inner channel. Examples of suitable materials include metals, alloys, plastics, composite materials or the like. As described above, a restriction ring may be used to prevent a tightened spiral from loosening, and the restriction ring may be sized and configured so that the spiral can conveniently slide into the restriction ring. The cannula may be part of a trocar or another delivery device. The plunger and the crimping sheet may be sized so that when the spiraled crimping sheet is inserted into the lumen of the cannula, a portion of the spiraled crimping sheet extends outside the lumen of the cannula, which can facilitate removal of the crimping sheet after the heart valve has been displaced from the spiraled crimping sheet into the cannula. The lumen of the cannula may have a projection protruding from the inner surface of the lumen, for abutting and stopping an inserted device such as the spiraled crimping sheet or the plunger.

In another embodiment, a method of crimping a prosthetic heart valve includes rolling a crimping sheet to form a spiral wrapped around the heart valve, manually tightening the spiral to compress the heart valve, inserting an end of the tightened spiral into a cannula, and displacing the heart valve out of the tightened spiral into the cannula.

Animal test results showed that mitral valves could be implanted with the procedure described herein in a short time, such as within 5 to 10 minutes. Thus, even if CPB is required, the CPB does not have to last for more than 5 to 10 minutes to implant the valve with the loading procedure described herein. The procedure could also be performed on a beating heart, and was short and simple. To implant an aortic valve, the prosthetic valve needed to be cooled to below room temperature and the heart needed to be arrested.

First, decalcification or removal of the pathologic valve was performed. Next, the prosthetic valve was loaded and implanted as described herein in a very short period and the procedure was simple and quick. The animal tests show that the prosthetic valve was holding well with no regurgitation. It was also shown that a sutureless valve may be efficiently delivered to a mitral position using a procedure as described herein.

As can be appreciated, kit 100 and a procedure disclosed herein may also be used to deliver other compressible devices other than heart valves.

Although it is convenient to use kit 100 to load a compressible device into a cannula or other tubing device, a valve or device with a suitable size matching the lumen size of the cannula can be loaded into the cannula using a crimping sheet and loading procedure described herein even if the valve or device is not substantially compressible. The crimping sheet can still be used to facilitate insertion of the valve or device into the cannula.

In different embodiments, a kit for crimping and loading heart valves or other devices does not need to include any cannula. For example, the kit may be designed to work with existing delivery devices that have a lumen for receiving the valve or device to be delivered, and have plungers and restriction rings that matching the size of the lumen.

It should also be understood that references to cannula and trocar herein are intended to broadly include any device that has a lumen and has a structure or configuration suitable for delivering a heart valve into another device or into a subject's body. Such a device can also be referred to as a delivery device herein. For example, such a delivery device may be include an implanter and may have a barrel. The implanter may be of a catheter type. The inner diameter of the barrel may range from about 5 mm to about 15 mm. The size of the barrel may be selected so that it can accommodate a prosthetic heart valve, which may have been deformed to reduced cross-section dimension, without compromising the durability and operation of the valve. The exterior of an implanter may include indicia (e.g., ruler markings) that can help indicate the distance the implanter is inserted into a patient. The implanter may be rigid. However, to facilitate positioning at a desired position, such as in a patient's heart, the implanter may include a tubular section that is formed of a flexible, generally resilient material (e.g., a metal or plastic material) that can bend or flex relative to its axial direction. For example, a barrel or cannula in the implanter may be formed of a helical extension spring, as described in U.S. Pat. No. 7,803,185. Alternatively or additionally, the cannula or barrel in the implanter may be formed of a deformable material, such as synthetic material (e.g., a polymer) or a metal, which is deformable to provide a desired curved cannula or barrel for supporting the heart valve for implantation.

A heart valve prosthesis to be crimped and loaded may be configured to have a fully expanded state and a compressed or contracted state. The prosthesis may be compressible when crimped and loaded into a cannula as described herein, and can expand toward its fully expanded state when it is discharged from the delivery device into a patient's heart, once the radial inward forces that maintain the prosthesis at a reduced cross-sectional dimension are removed. The prosthesis may include a self-expanding support in which an associated heart valve is mounted, e.g. as described in U.S. Pat. No. 7,803,185. As the prosthesis is being discharged, the implanter can be concurrently withdrawn.

As can be appreciated with a flexible delivery device or implanter, a heart valve may be implanted without opening the heart of the patient and without CPB. It is also possible to implant a heart valve in a short open chest surgery with reduced CPB as compared to conventional processes, with or without sutures.

It will be understood that any range of values herein is intended to specifically include any intermediate value or sub-range within the given range, and all such intermediate values and sub-ranges are individually and specifically disclosed.

It will also be understood that the word "a" or "an" is intended to mean "one or more" or "at least one", and any singular form is intended to include plurals herein, unless expressly specified otherwise.

It will be further understood that the term "comprise", including any variation thereof, is intended to be open-ended and means "include, but not limited to," unless otherwise specifically indicated to the contrary.

When a list of items is given herein with an "or" before the last item, any one of the listed items or any suitable combination of two or more of the listed items may be selected and used.

Of course, the above described example embodiments of the present disclosure are intended to be illustrative only and in no way limiting. The described embodiments are susceptible to many modifications of form, arrangement of parts, details and order of operation. The invention, rather, is intended to encompass all such modification within its scope, as defined by the claims, which should be given a broad interpretation consistent with the description as a whole.

What is claimed is:

1. A crimping and loading kit, comprising:
a prosthetic heart valve;
a crimping sheet foldable to form a spiral wrapped around the prosthetic heart valve, said spiral manually rollable and tightenable to compress the prosthetic heart valve wrapped inside said spiral, so that the tightened spiral is slidably insertable into a lumen of a cannula for delivering the prosthetic heart valve;
a plunger sized for insertion into said tightened spiral to displace the prosthetic heart valve out of the spiral and into said lumen of said cannula; and
a restriction ring sized to slide over said tightened spiral to prevent loosening of the tightened spiral.

2. The kit of claim 1, further comprising said cannula, wherein said lumen of said cannula is sized to house the compressed heart valve.

3. The kit of claim 1, wherein said crimping sheet comprises a metal or a plastic.

4. The kit of claim 1, wherein said crimping sheet has a thickness of less than 1 mm.

5. The kit of claim 1, wherein said cannula is in a trocar.

6. The kit of claim 1, wherein said lumen of said cannula has a diameter from 1 mm to 40 mm.

7. The kit of claim 1 comprising a plurality of cannulas having different lumen diameters.

8. The kit of claim 7, wherein the lumen diameters are selected from 18, 21, 23, 24, 25, 27, 29, 31, 33, and 35 mm.

9. The kit of claim 1, wherein the heart valve is a stented sutureless mitral, aortic, tricuspid, or pulmonic valve.

* * * * *